(12) United States Patent
Casarotto et al.

(10) Patent No.: US 11,975,173 B2
(45) Date of Patent: May 7, 2024

(54) LIQUID FLOW REGULATION DEVICE

(71) Applicant: PHOENIX R&D S.R.L., Rovigo (IT)

(72) Inventors: Luciano Casarotto, Rovigo (IT);
Michele Maggiolo, Frassinelle Polesine (IT); Fiorenzo Casarotto, Villamarzana (IT); Leobaldo Casarotto, Rovigo (IT)

(73) Assignee: PHOENIX R&D S.R.L., Rovigo (IT)

( * ) Notice: Subject to any disclaimer, the term of this patent is extended or adjusted under 35 U.S.C. 154(b) by 965 days.

(21) Appl. No.: 16/959,458

(22) PCT Filed: Jan. 9, 2019

(86) PCT No.: PCT/IB2019/050160
§ 371 (c)(1),
(2) Date: Jul. 1, 2020

(87) PCT Pub. No.: WO2019/142071
PCT Pub. Date: Jul. 25, 2019

(65) Prior Publication Data
US 2021/0069414 A1     Mar. 11, 2021

(30) Foreign Application Priority Data

Jan. 16, 2018   (IT) .................. 102018000001067
Apr. 24, 2018   (IT) .................. 102018000004826

(51) Int. Cl.
*A61M 5/168*   (2006.01)
*A61M 5/14*    (2006.01)

(52) U.S. Cl.
CPC . *A61M 5/16813* (2013.01); *A61M 2005/1402* (2013.01); *A61M 2205/582* (2013.01)

(58) Field of Classification Search
CPC .......... A61M 5/16877; A61M 5/16881; A61M 5/16804
See application file for complete search history.

(56) References Cited

U.S. PATENT DOCUMENTS

| | | |
|---|---|---|
| 2,911,008 A | 11/1959 | Du Bois |
| 2003/0097097 A1 | 5/2003 | Scagliarini et al. |
| 2005/0065480 A1* | 3/2005 | Lee .................. A61M 5/16881 604/246 |
| 2007/0018129 A1 | 1/2007 | Guala |
| 2008/0097097 A1 | 4/2008 | Ragan |
| 2013/0178805 A1 | 7/2013 | Baid |
| 2016/0106913 A1 | 4/2016 | Ng et al. |

* cited by examiner

*Primary Examiner* — Deanna K Hall
(74) *Attorney, Agent, or Firm* — Dickinson Wright PLLC; Andrew D. Dorisio (57) ABSTRACT

A device which regulates the flow of a medical liquid includes a first and a second body, the first body featuring a first passage fluidly connected to a regulation channel, the second body featuring a second passage which may be positioned at a desired point of the regulation channel and set, during use, in fluid passage communication with the first passage by means of the regulation channel. The device includes a limiter which, once engaged, can no longer be disengaged during normal use of the regulation device, the first body or the second body featuring at least a first stop, and the limiter, when engaged, encountering the first stop in order to prevent the second passage being positioned in a predetermined portion of the regulation channel and/or at the first passage.

16 Claims, 6 Drawing Sheets

LIQUID FLOW REGULATION DEVICE

The present invention concerns a liquid flow regulation device, possibly for liquids with semisolid particles in suspension.

In particular, the invention concerns a device which regulates the flow of liquids used in the medical field.

In the medical field, the administration of liquids, such as intravenous solutions, is carried out though the use of various devices, including:
  pressure sets connected to electronic infusion pumps
  gravity sets regulated by roller clamps
  gravity sets with flow regulators

FIELD OF THE INVENTION

A set is an assembly of components connected to a flexible tube whose function is to fluidly connect the container holding the solution to be administered to one of the patient's veins. The standard components comprise a perforator, which penetrates the cap sealing the container and allows the solution to enter the tubular line; a dropper chamber, which prevents the passage of air bubbles with the solution and allows flow monitoring; a device, such as a roller clamp or a flow regulator, for flow control; and finally, the cannula needle, which allows the solution to flow from the tubular line into the patient's vein. Other components, such as filters, taps, and connectors, may be added to the set for the management of supplementary functions.

BACKGROUND OF THE INVENTION

During use, the infusion set must be prepared prior to connection thereof to the patient for administration. During such preparation, it is essential to fill the tubular line with fluid completely and to ensure all the air previously contained has been expelled, to prevent the risk of embolism for the patient. To ensure the effectiveness of this operation, it is essential that the flow rate of the fluid inside the line be very high. Such high flow rate also reduces the time required for the said operation. Standard ISO 8536-4 establishes a minimum value for this flow rate (known as "free-flow") of 6000 ml/h in the reference conditions. Once the set is filled, the flow must be stopped to allow the needle to be inserted into the patient's vein, after which administration is resumed at a much lower flow rate, generally less than 300 ml/h. Over the course of the treatment, it will no longer be necessary to return to the free-flow rate, which must be avoided at all costs in order not to endanger the patient's health. All hospital staff are well aware of this risk and work diligently to prevent the realisation thereof.

Among flow control components, flow regulators are particularly significant. Such components were the last to be introduced on the market (in the mid-70s in the United States) and since then they have become increasingly widespread the world over.

They guarantee far superior accuracy and reliability than that provided by roller clamps. They also have lower operating costs than the pumps and are much simpler to use.

During the set preparation stage, the regulator is placed in a fully open position. Often the fully open position is already set by default in the factory, so as to automatically ensure maximum flow once the regulator is supplied with the solution to be administered.

DESCRIPTION OF THE INVENTION

Once the preparation phase is over, the operator (usually a nurse or a doctor) rotates or moves a component of the regulator to stop the flow and connect the set to the patient, then uses the said component once again to achieve the desired volumetric flow within the unit of time.

Often the adjustment is performed using an adjustment scale featured on the said regulator.

One typical drawback of commonly known flow regulators is that they are easily tampered with (possibly unintentionally) by the patient.

Since the administration of the fluid can last a considerable length of time, it is possible that the patient may move the regulator, possibly inadvertently, thereby changing the flow of the substance set by the operator.

If the regulator is tampered with and the solution flow rate decreased, the patient generally does not suffer any serious damage. Indeed, upon subsequently checking the patient, the operator realises that the substance has not been administered fully and therefore resumes administration by resetting the regulator.

It is quite another case, however, if the regulator is moved by the patient to the maximum opening position. This possibility is extremely dangerous for the patient's health. Certain studies have shown that some kinds of patients, such as children or the elderly with senile dementia, tend to behave in ways which could lead to them tampering with the regulator, thereby putting their own safety at risk.

The object of the present invention is to provide a regulator which is safer than those which are commonly known.

A further object is to provide a regulator which can no longer be returned to the fully open (maximum flow) position following insertion of a safety device after initial adjustment.

This and other objects are achieved by means of a liquid flow regulation device produced according to the technical teachings of the claims annexed hereto.

BRIEF DESCRIPTION OF THE DRAWING FIGURE

Further characteristics and advantages of the invention will become clearer in the description of a preferred but not exclusive embodiment of the device, illustrated—by way of a non-limiting example—in the drawings annexed hereto, in which.

With reference to the figures stated, reference number 1 is used to denote, as a whole, a liquid flow regulation device.

Figure 1:
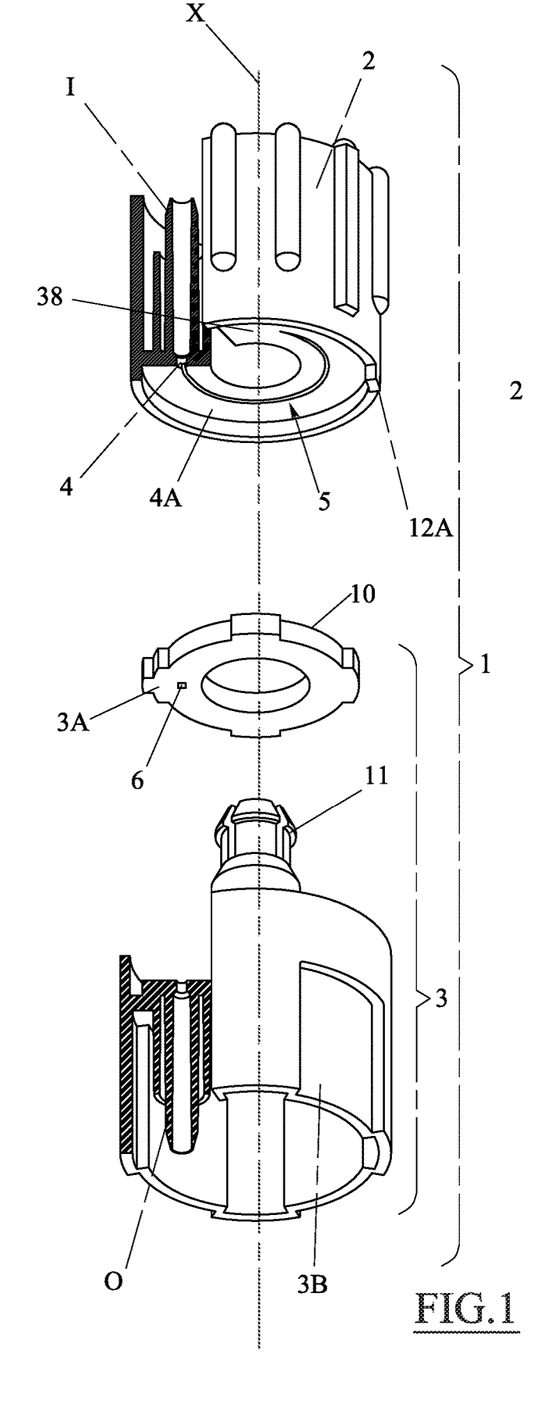
FIG. 1 is a simplified exploded view of a regulation device according to the present invention.

FIG. 1 shows an exploded view of the device 1 used to regulate the flow of a medical liquid.

In the present description, the medical liquid is generally a solution for intravenous administration, such as saline, glucose, isotonic, lipid and other solutions, but the liquid may also be intended to feed a patient, by means of a cannula or nasogastric tube or suchlike.

Figure 18:
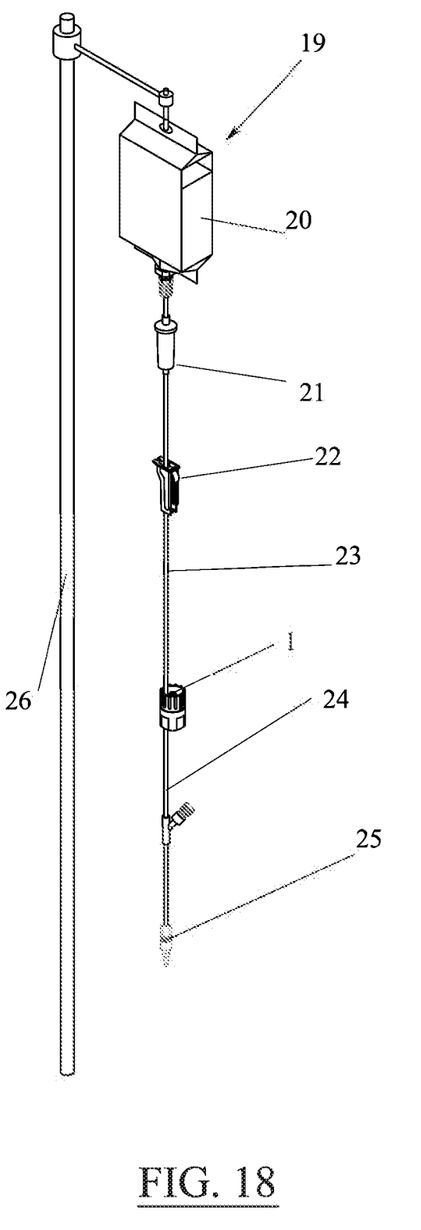
FIG. 18 shows an example of use of a regulator according to the present invention.

FIG. 18 shows a system 19 for the administration of a solution contained in a bag 20. The bag 20 is connected to a drip chamber 21, from which a first tube 23 extends which may be intercepted with a clamp 22. The tube 23 is connected to an intake I on the device 1. A second tube 24 is connected to an outlet O on the device and, in the example, it is coupled to a connector 25 which provides access to the cannula needle.

Obviously, the configuration illustrated is provided merely for exemplification purposes and, when in use, the regulator may be coupled (depending on the different use requirements) to other systems, tubes, solution containers etc. which are suitable for the fluid to be administered.

With reference to FIG. 1, note that the device 1 comprises a first body 2 and a second body 3, which are mutually connected. As mentioned earlier, the first body 2 features an intake I, which is conventionally configured to be coupled to the tube 23.

Obviously, other configurations may be envisaged for the intake I, all of which would be obvious to a person skilled in the art. The intake I is fluidly associated with a first passage 4, which—in turn—is fluidly connected to a regulation channel 5. As mentioned earlier, the regulation channel 5 may be conventionally envisaged with a variable section or as described in patent application WO2017118897-A1, to which reference should be made.

Figure 11:
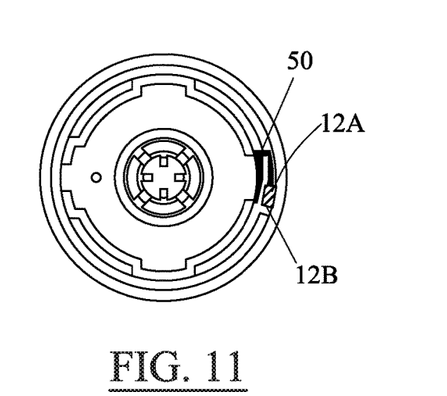
FIGS. 11 to 13 show, schematically, in a partially sectioned and simplified bottom-up view, an alternative embodiment of the limiter, in positions in which it is—respectively—deactivated, close to engagement, and engaged.

Note that the first body 2 is preferably made by moulding a single piece of medical grade plastic, such as ABS, PP or PC. As can be seen in FIG. 11, however, the said component may also be made from several pieces, as is conventional in the field of flow regulators.

The second body 3 features a second passage 6, which can be positioned at a desired point of the regulation channel 5 and in fluid passage communication with the first passage 4 through the very same regulation channel 5.

In the configuration illustrated, the second passage 6 is made of a gasket 3A which is torsionally associated with an element 3B, which is preferably moulded from a single piece of the same plastic as used for the first body.

The material of which the gasket 3A is made, meanwhile, is an elastomer.

It must be said that in the present configuration, the gasket 3A and the element 3B are two separate parts. However, a second body 3 may be envisaged which is made as a single piece, for example using overmoulding techniques. Alternatively, element 3B may also be made of several parts.

In practice, the only important requirement is that the surface 10 of the second body 3—which is designed to encounter a free surface 4A of the first body (where the regulation channel 5 is located, which is open in correspondence with the said free surface)—is capable of forming a seal on the said surface, at least when the first and second bodies are mutually coupled.

In the example illustrated, the coupling between the first body 2 and the second body 3 may feature flexible teeth 11 which, by engaging—by means of an undercut, snap mechanism—with a corresponding portion of the first body 2, allows the first body to rotate with respect to the second one around axis X. There are stops 12A, 12B (or teeth) featured between the first body 2 and the second body 3, which can limit the relative rotation of the two bodies between predetermined stroke limit positions.

The rotation of the first body 2 with respect to the second 3 (or vice versa) allows the second passage 6 to be positioned at any point (subject to the design specifications) of the regulation channel 5, which is open at the interface surface between the first and the second body.

In this way, the first passage 4 (which can be formed at one end of the regulation channel 5) and the second passage 6 are fluidly connected through the very same regulation channel 5. The length of the stretch of the regulation channel separating the first passage from the second may vary according to the reciprocal position of the first and second elements, so as to regulate the flow running through the device 1.

Figure 6:
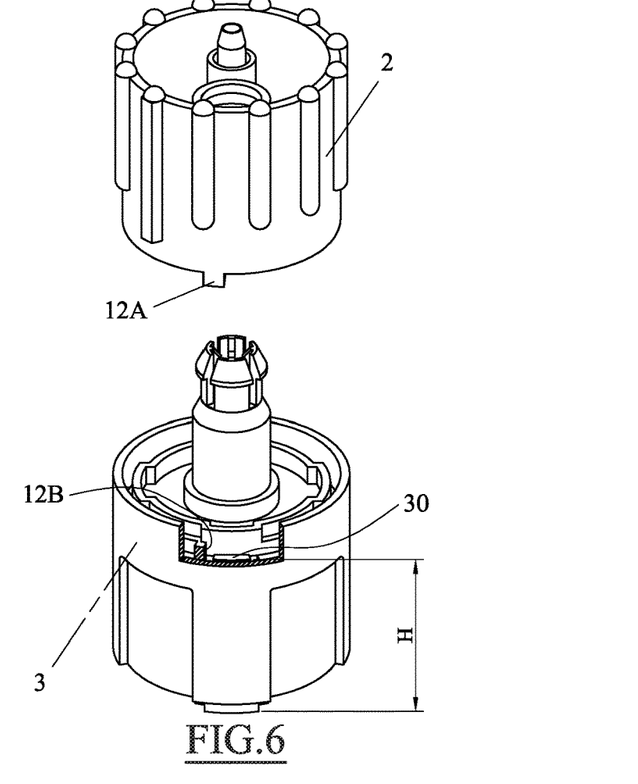
FIG. 6 is an exploded perspective view, with certain parts removed for the sake of clarity, which highlights the disengaged limiter.
Figure 9:
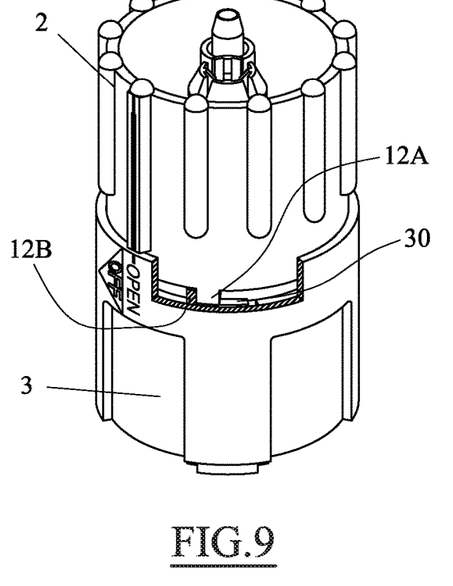
FIGS. 9 and 10 show the operation of the limiter, first in the disengaged position and then engaged: the limiter is visible through a cut-away section of a side wall of the regulator.

As already mentioned, the first body 2 features a first stop 12A, which, during use, encounters a second stop 12B featured on the second body 3 (which is clearly visible in FIG. 6, and in FIG. 9, where the first and the second stop are in contact).

The first and the second stop (or teeth) limit the mutual rotation between the first and the second body.

In practice, when the first and second teeth are in contact, as shown in FIG. 9, the second passage 6 is superimposed on the first passage 4 and the regulator is in the maximum flow position. In this condition, the regulation channel 5 does not influence the flow of the said fluid, since there is a direct communication between the first and the second passage.

This condition is useful for the preparation (priming) of the infusion set.

According to the present invention, during normal use of the regulator, the regulator comprises an irreversible limiter 30, 50 which, once engaged, can no longer be disengaged by the patient and prevents the second passage 6 being positioned in a predetermined stretch of the regulation channel 5.

More specifically, once engaged, the limiter prevents the first passage 6 being re-positioned at an initial part of the regulation channel 5, where the first passage 4 is formed. In practice, once the limiter has been engaged, it is impossible to set the regulator in a fully open position, which would correspond to a maximum flow condition.

Preferably, when engaged, the limiter is positioned between the first and the second stop so as to prevent the first stop 12A from encountering the second stop 12B.

Figure 5:
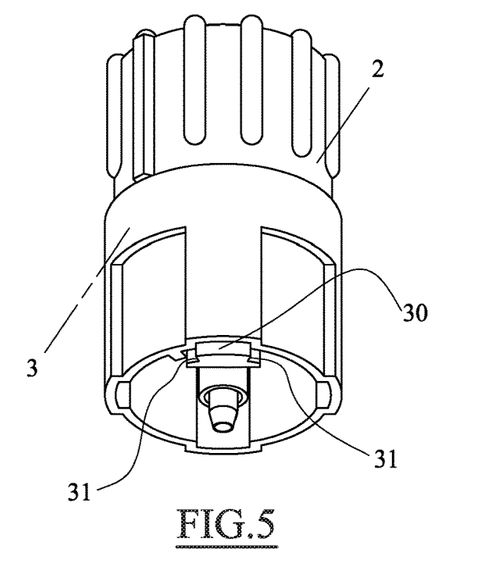
FIG. 5 is a bottom-up perspective view of the regulator in FIG. 2 with a limiter disengaged.

In FIGS. 5 to 10, note that the limiter may be a slide 30 associated with the second body 3, which is accessible (from the bottom of the regulator as shown in FIG. 5, in which the limiter is disengaged) and movable—in a simple manner (by applying pressure upwards in the figure)—only when in the disengaged position.

In FIG. 6, it can be seen that the slide 30 (shown in the lowered position and therefore with the limiter disengaged) is positioned near the second stop 12B (on the second body 3).

In practice, the slide 30 may feature guides 31, which cooperate with counter-guides 32 on the second body 3. Preferably, the guides and the counter-guides allow a dovetail coupling.

Furthermore, there is a friction and/or interlocking coupling between the slide 30 and the second body 3 so that when the slide is pushed upwards (FIG. 8), it remains in that position as a result of the said friction and/or interlock.

Optionally, the slide 30 may feature a snap mechanism system (for example a tooth or other kind of undercut) which keeps it locked in the engagement position, once limiter engagement has occurred.

Figure 17:
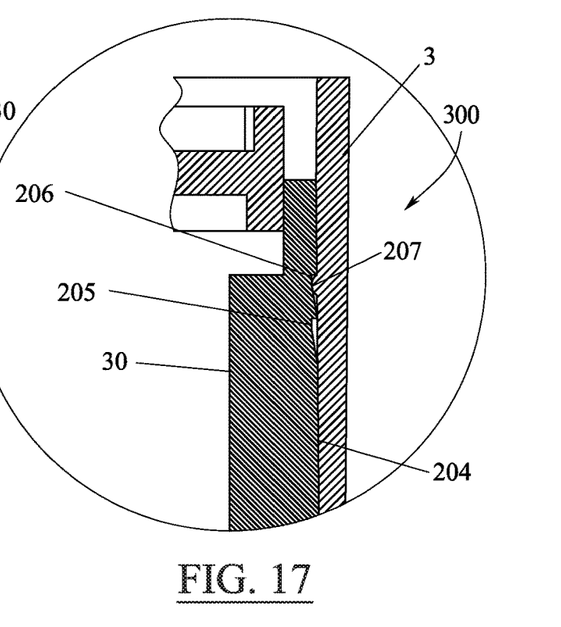
FIG. 17 is a simplified enlargement of the section in FIG. 16.

One example of such a snap mechanism system is provided for exemplification purposes in FIG. 17. In this solution, there is a snap mechanism stabilisation system 300 between the limiter 30 and the second body 3, which permanently secures the limiter when in the said engaged position and/or the said disengaged position.

More specifically, on a surface 204 of the limiter in contact with the second body 3, there are recesses 205, 206 (at least one, envisaged for the engagement position, but preferably two, with one for the engagement position and one for the disengaged position) which engage alternatively with a protuberance 207 present on the second body 3, when the limiter 30 is in an engaged or disengaged position.

In this way, upon engaging the limiter 30, the user feels a 'click', which confirms the activation thereof in a stable engagement position.

However, when the limiter 30 is in a disengaged position, and therefore slightly protruding from an edge of the second body 3, the presence of the system prevents the limiter being disengaged from the second body 3.

Slightly earlier, it was disclosed how recesses 205, 206 may be provided in the limiter with which a protuberance on the second body 3 engages. Obviously, in one variant, the situation may be symmetrical, with the recesses provided on the body 3 while the protuberance(s) may be provided on the limiter.

Figure 7:
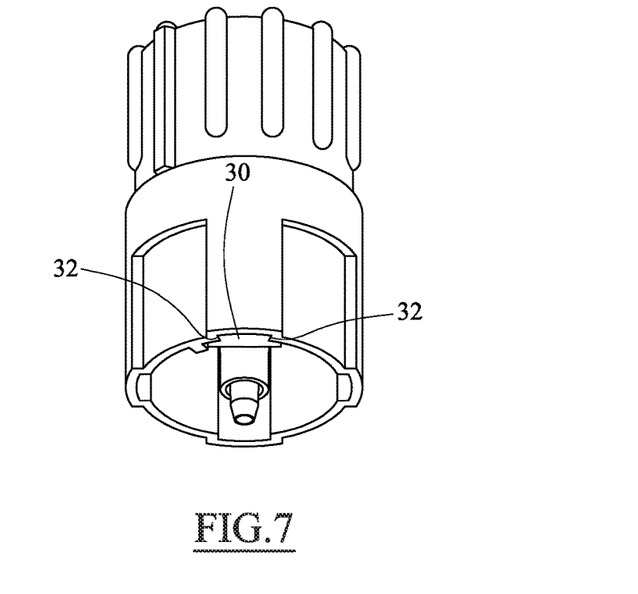
FIG. 7 is a bottom-up perspective view of the regulator in FIG. 2 with a limiter engaged.
Figure 8:
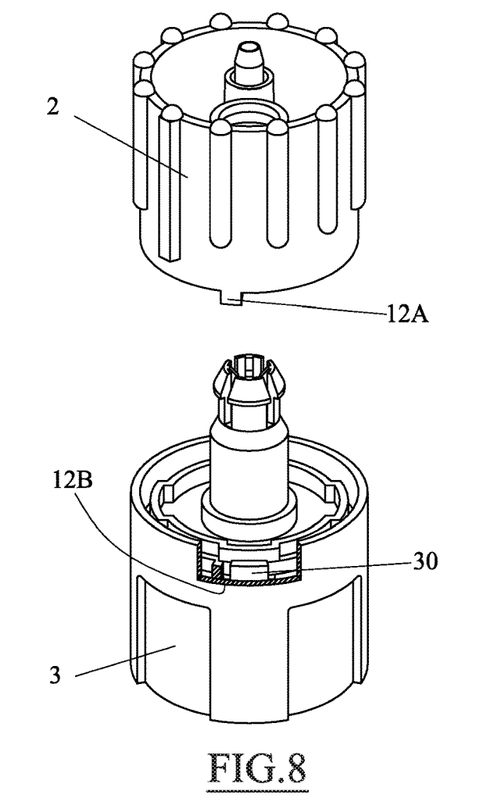
FIG. 8 is an exploded perspective view, with certain parts removed for the sake of clarity, which highlights the engaged limiter.

In FIG. 7, it can be seen that the height H of the slide 30 is such that, when the limiter is engaged, one edge thereof is flush with one edge of the second body 3.

In this way, once the slide is pushed upwards, so that the limiter is active, it is no longer possible to move it down, without the aid of an external tool or, more simply, during normal use, as the slide is no longer directly accessible.

It must be said that in certain emergency situations or in other unforeseen events, it may be necessary to reset the regulator in its maximum flow position. For this reason, the limiter 30 features an external tool 201 hook-up area 200, which allows, for example a nurse (but not a patient) to release the limiter following the engagement thereof.

In one example, the hook-up area 200 may comprise a recess (or a relief) located on a surface 202 which is either hidden or difficult to access during normal device use.

For example, the surface 202 on which the hooking region is provided may be facing the central internal part of the second body 3 of the regulator.

In this way, this surface 202 is not easily accessible during normal use of the regulator and certainly is not accessible by a patient who, intentionally or otherwise, attempts to set the regulator back in its maximum opening position.

Advantageously, once the limiter has been engaged for the first time, the regulator, may be released, for example with the aid of an external tool (for example one equipped with a hook, such as a folded paper clip or a special tool (201), which—when used with expertise by a nurse—can release the limiter 30. Continuing with the description of the invention, note that the slide is wide enough to isolate, with the limiter activated, a varying stretch of the regulation channel 5, close to the first opening 4.

The description above states that the slide is advantageously endowed with a recess. This recess may be used to insert a tool, the tip of something, etc. to release the regulator. In this configuration, the accessible part of the slide is essentially smooth and has devoid of reliefs so as not to offer a grip to anybody attempting to release the regulator.

If, on the other hand, there were a relief on the slide, release would be possible without any tool. However, in this case, the relief should be located in a part of the slide which is either hidden or difficult to access, so that release is impossible by an untrained user, or by a user who is not familiar with the details of the regulator. Essentially, the slide is configured to make release difficult, in particular if the user is not familiar with the operation of the regulator.

Figure 3:
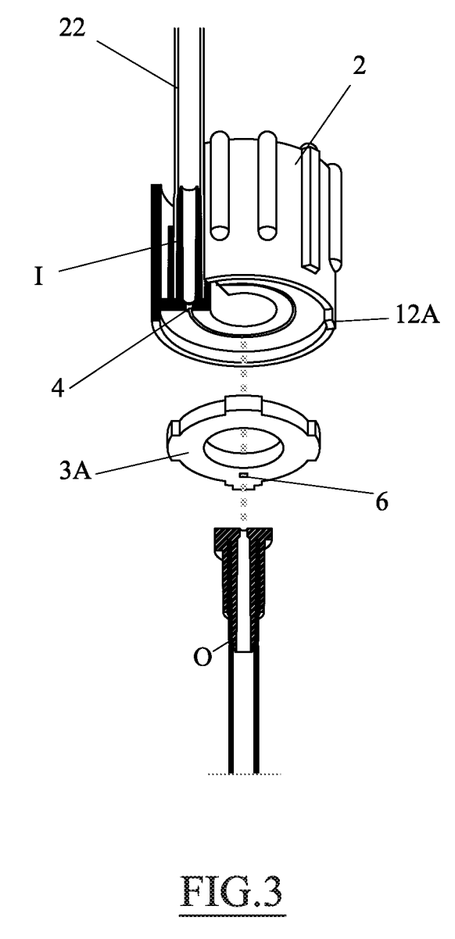
FIGS. 3 and 4 show, schematically, a cut-away view of the regulator in two different operating positions.
Figure 4:
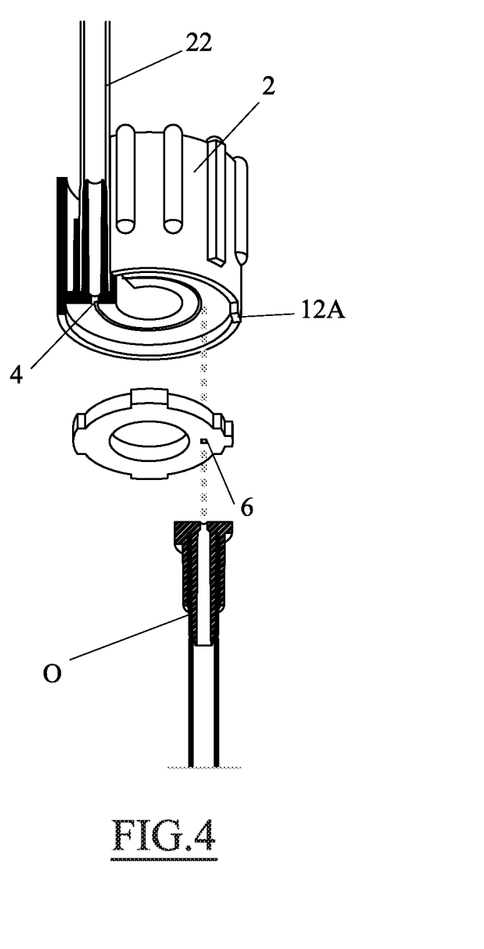

The operation of the invention is obvious from the foregoing for those skilled in the art and will now be illustrated with particular reference to FIGS. 3 and 4.

A flow of a liquid is supplied under pressure (by gravity, for example) to the intake I on the device 1. The liquid flows through the first passage 4 and along the regulation channel 5 until reaching the second passage 6, and from there, the outlet O.

With the limiter disengaged, by rotating the second element 3 with respect to the first 2 (or vice versa), the second passage may be positioned in any point (subject to design limits) of the regulation channel 5. In this way, the stretch of the regulation channel 5 affected by the moving fluid may have a variable length (see FIG. 3, short stretch, and FIG. 4, longer stretch) depending on the mutual angle of the first and second elements. The length of the regulation channel 5 and the section thereof at the outlet point determine the flow rate of the fluid in a conventional manner.

Figure 2:
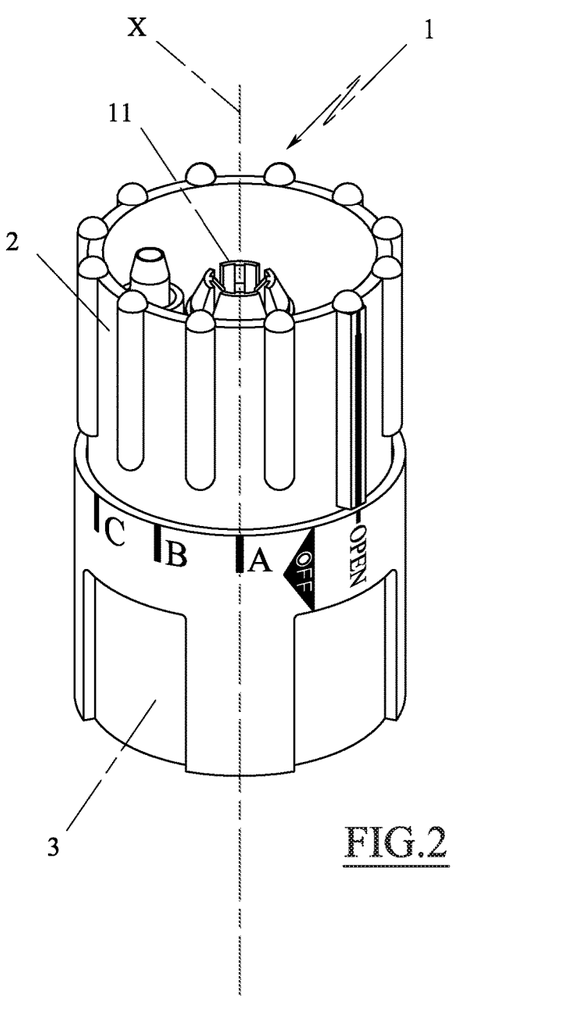
FIG. 2 is a perspective view of the device in FIG. 1, when assembled.

The length of the stretch of the regulation channel 5 and the section thereof at the outlet point determine the loss of flow load of the liquid or fluid. This allows the flow to be slowed (and therefore regulated) in a controlled manner depending on the angular position of the first body with respect to the second. As can be seen from FIG. 2, the device may feature printed references (A, B, C) which refer to the flow volume delivered during the unit of time by the device with the first body in a given angular position with respect to the second. Advantageously, the positions are discrete as shown in FIG. 2.

It should be noted, for example, that the OPEN position (OPEN) is obtained when the second passage 6 is superimposed over the first passage 4, and therefore, in practice, there is no circulation of fluid inside the regulation channel 5.

The OFF position (CLOSED) is obtained, meanwhile, by moving the second passage 6 into a zone 38 of the surface 4A of the first body 2, beyond the end of the channel 5.

Figure 10:
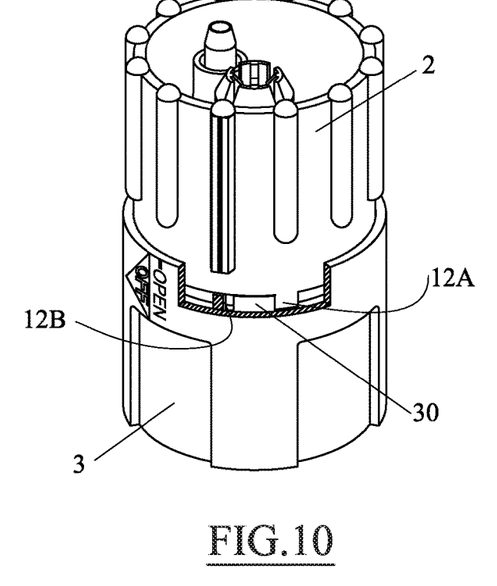

The operation of the limiter is easily understood from a comparative analysis of FIGS. 9 and 10. In FIG. 9, the limiter is disengaged and the slide 30 is lowered. From the bottom of the regulator (in FIG. 9), there protrudes a part of the slide 30 which is accessible from the outside.

In this configuration, a relative rotation of the first body with respect to the second one is enabled without further limitations apart from those imposed by the first and second stops 12A, 12B when in mutual contact. More specifically, in this configuration, the first stop 12A can run over the slide 30, without interfering with the movement thereof, until the said stop encounters the second stop 12B, bringing the regulator into the maximum opening position thereof.

Once administration has been started and the flow rate has been adjusted by rotating the first body 2 with respect to the second 3, the limiter can be engaged by pushing the slide 30 upwards, so that the said slide no longer protrudes from the lower edge of the regulator.

Obviously, in order to perform this operation, the first stop 12A must be out of the range of movement of the slide 30. For example, the slide may be engaged when the regulator is closed, or when the flow rate is very low.

When the limiter is engaged, if someone attempts to set the regulator back in the maximum opening position, the first stop 12A encounters the slide 30, which therefore prevents rotation.

Therefore, once the limiter is engaged, a patient can no longer tamper with the regulator, e.g. adjusting the regulator and returning it to the maximum opening position.

Furthermore, the engagement of the limiter is irreversible for a patient, and once engaged, the limiter can no longer be deactivated without the use of an external tool, or in any way which could be imagined by a patient or a person who is not familiar with who the regulator is operated.

In the configuration described, the irreversibility (for the patient) of the limiter is achieved by calibrating the height of the slide so that, when the limiter is engaged, the slide is no longer accessible from outside the regulator.

Figure 12:
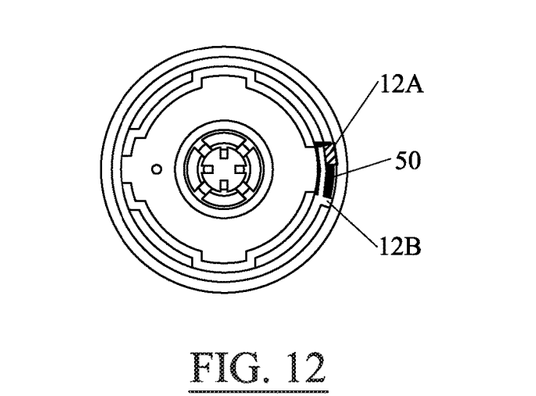
Figure 13:
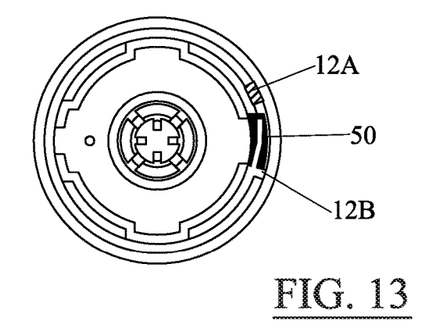
Figure 14:
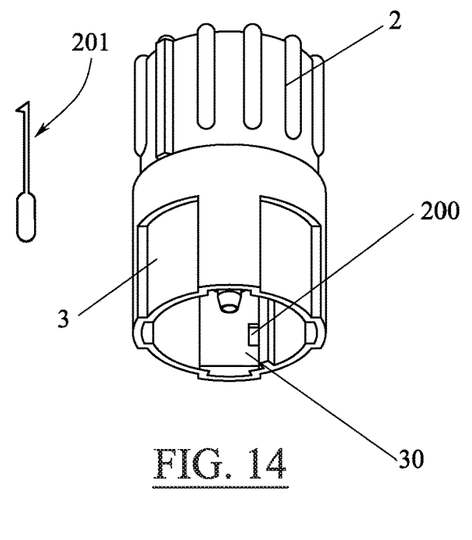
FIG. 14 shows a detail of a variant of the regulator in FIG. 1.
Figure 15:
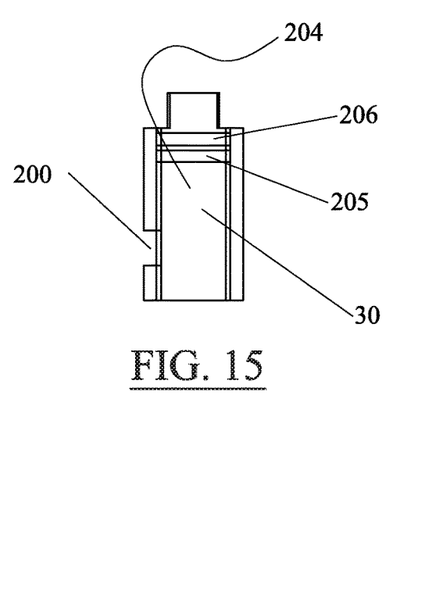
FIG. 15 shows a detail of the regulator in FIG. 14.
Figure 16:
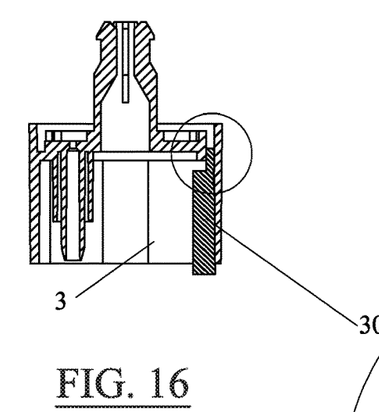
FIG. 16 shows a section of a possible variant of the regulator in FIGS. 1 and 14.

FIGS. 11 to 13 show a possible variant of the limiter according to the present invention. In these figures, note that the limiter is an elastic element 50 (elastic clip) which activates when the regulator is moved out of the maximum flow position, so as to stop the movement of the first stop 12A before the said stop comes into contact with the second stop 12B.

In practice, the elastic element 50 may be a sturdy clip or tab, for example with a U-shaped section. The elastic element may assume any conformation which is useful for the purpose, however the said element is preferably positioned between the first and second stops.

When the regulator is in a maximum flow position, a flexible tab on the elastic element 50 is compressed by the first stop 12A, and the first stop comes into contact with the second stop 12B. This is the position in which the regulator is set when supplied.

After priming, when the regulator is moved to an intermediate flow position, the first stop 12A slides over the elastic element 50 and as soon as the latter is no longer compressed by the stop, the tab thereof clicks into the uncompressed position, interposed between the first stop 12A and the second stop 12B in order to limit rotation, as in the previous case. It this condition, it is impossible to reset the regulator in the maximum opening position.

Various embodiments of the innovation have been disclosed herein, but further embodiments may also be conceived using the same innovative concept. In this way, for example, it is possible to design a regulation channel which extends in a substantially rectilinear fashion. In this case, the positioning of the second passage with respect to the channel may be obtained by simply moving a suitably configured slider within which the second passage is formed.

The invention claimed is:

1. A device (1) which regulates the flow of a medical liquid, comprising a first (2) and a second body (3), the first body (2) having a first passage (4) which is fluidly connected to a regulation channel (5), the second body having a second passage (6) which may be positioned at a desired point of the regulation channel (5) and set, during use, in fluid passage communication with the first passage (4) by the regulation channel (5), the said device comprising a limiter (30, 50) which, once engaged, can no longer be disengaged during normal use of the regulation device, the first body (2) or the second body (3) having at least a first stop (12A), the limiter (30, 50), when engaged, encountering the first stop (12A) in order to prevent the second passage (6) being positioned in a predetermined portion of the regulation channel (5) or at the first passage (4).

2. A device (1) according to claim 1, in which the limiter is a slide (30), associated with the second body (3), the said slide being directly accessible and movable only when in the disengaged position.

3. Device (1) according to claim 2, wherein the first body (2) and the second body (3) feature at least a first (12A) and a second stop (12B), and the limiter (30), when engaged, is interposed between the first and second stop so as to prevent the first stop encountering the second stop.

4. A device according to claim 3, in which the second stop (12B) is associated with the second body (3), the slide (30) being positioned in proximity to the second stop (12B).

5. A device according to claim 3, in which the slide (30) comprises guides (31) which cooperate with counter-guides (32) on the second body (3) or in which the guides and the counter-guides form a dovetail coupling.

6. A device according to claim 2, in which the height (H) of the slide (30) is such that, when the limiter is engaged, one edge thereof is flush with one edge of the second body (3).

7. A device according to claim 2, in which the slide (30) comprise an external tool (201) hook-up area (200), for releasing the limiter following the engagement thereof.

8. A device according to claim 7, in which the hook-up area (200) comprises a recess located on a surface (202) which is hidden during normal device use.

9. A device according to claim 7, in which—with the exception of the recess (200)—the accessible part of the slide (30) is free of grips, or in which the hook-up area (200) features a relief.

10. A device according to claim 2, in which there is a snap mechanism stabilization system (300) between the slide (30) and the second body (3), which stably secures the limiter when in the said engaged position and/or in the said disengaged position.

11. A device according to claim 1, in which the limiter (30, 50) is an elastic element (50) which activates when the regulator is moved out of the maximum flow position, so as to encounter the first stop (12A).

12. A device according to claim 11, in which—when the regulator is a maximum flow position—the elastic element (50) is urged into a compressed position by first stop (12A).

13. A device according to claim 1, wherein the regulation channel is recessed with respect to a free surface (4A) of the first body (2) and open on said free surface.

14. A device according to claim 1, in which a gasket (3A)—where the said second passage (6) is formed—is fixed to the second body (3), the gasket being configured to rest and seal on the free surface (4A) of the first body (2) when the first and second bodies (3) are coupled.

15. A device according to claim 1, in which the first (2) and the second body (3) are rotatably connected, so that mutual rotation around a common axis (X) positions the second passage (6) at any point along the regulation channel (5) when the limiter is deactivated.

16. A device according to claim 1, wherein the limiter is movable between a disengaged position to an engaged position, the engaged position blocks rotation of the first body relative to the second body, and the disengaged position allows rotation of the first body relative to the second body.

\* \* \* \* \*

UNITED STATES PATENT AND TRADEMARK OFFICE
CERTIFICATE OF CORRECTION

| | | |
|---|---|---|
| PATENT NO. | : 11,975,173 B2 | Page 1 of 1 |
| APPLICATION NO. | : 16/959458 | |
| DATED | : May 7, 2024 | |
| INVENTOR(S) | : Casarotto et al. | |

It is certified that error appears in the above-identified patent and that said Letters Patent is hereby corrected as shown below:

On the Title Page

Item (72) Inventors:
After "Luciano Casarotto, Rovigo(IT); Michele Maggiolo, FrassinellePolesine (IT); FiorenzoCasarotto, Villamarzana (IT); Leobaldo Casarotto, Rovigo(IT)"
Insert --Daewon KANG, Rovigo(IT)--

Signed and Sealed this
Fourteenth Day of October, 2025

John A. Squires
*Director of the United States Patent and Trademark Office*